United States Patent [19]

Danziger et al.

[11] 4,170,592

[45] Oct. 9, 1979

[54] PURIFICATION OF ε-CAPROLACTAM

[75] Inventors: Harry Danziger; Bernd-Ulrich Kaiser, both of Krefeld, Fed. Rep. of Germany; Guido Rampart, Ekeren, Belgium; Jürgen Schröter, Krefeld, Fed. Rep. of Germany

[73] Assignee: Bayer Aktiengesellschaft, Fed. Rep. of Germany

[21] Appl. No.: 832,007

[22] Filed: Sep. 9, 1977

[30] Foreign Application Priority Data

Sep. 15, 1976 [DE] Fed. Rep. of Germany ....... 2641449

[51] Int. Cl.$^2$ .......................................... C07D 201/16
[52] U.S. Cl. ............................................. 260/239.3 A
[58] Field of Search ................................ 260/239.3 A

[56] References Cited

U.S. PATENT DOCUMENTS

| | | | |
|---|---|---|---|
| 2,758,991 | 8/1956 | Kretzers et al. | 260/239.3 A |
| 3,761,467 | 9/1973 | Williams et al. | 260/239.3 A |
| 4,036,830 | 7/1977 | De Rooij et al. | 260/239.3 A |

Primary Examiner—Natalie Trousof
Assistant Examiner—Robert T. Bond
Attorney, Agent, or Firm—Connolly and Hutz

[57] ABSTRACT

A process for the purification of a solution of ε-caprolactam in benzene, toluene or xylene by washing with a liquid, wherein the washing liquid is a solution of ε-caprolactam in water in a weight ratio of from 15 : 1 to 1 : 3, which is used in a quantity of from 5 to 20% by weight, based on the solution of caprolactam in benzene, toluene or xylene, and wherein there are several washing stages so that the equilibrium between the two solutions can be readjusted.

1 Claim, No Drawings

PURIFICATION OF ε-CAPROLACTAM

In the preparation of ε-caprolactam, for example by the Beckmann rearrangement of cyclohexanone oxime or by the catalytic rearrangement of cyclohexanone oxime in the gaseous phase, the ε-caprolactam obtained is frequently extracted with benzene or similar solvents such as toluene or xylene. Solutions of ε-caprolactam in these organic solvents are then obtained. These must be purified and worked up. In some cases, these solutions have been washed with dilute sulphuric acid, dilute sodium hydroxide solution or water (German Auslegeschrift No. 1,031,308). However, the sodium hydroxide or sulphuric acid is then carried into the next stage of purification. Washing with water also did not prove to be very effective. Attempts have been made to extract all the ε-caprolactam from the organic solution with water. Although a high degree of purity is obtained with this method, the water must be removed from the caprolactam, and this requires considerable technical expenditure.

The present invention provides a process for the purification of a solution of ε-caprolactam in benzene, toluene or xylene by washing with a liquid, wherein the washing liquid consists of ε-caprolactam dissolved in water in a proportion by weight of from 15:1 to 1:3, this washing liquid being used in a quantity of from 5% to 50% by weight, based on the caprolactam solution in benzene, toluene or xylene, and in that washing is carried out in several stages so that the equilibrium between the two solutions can be repeatedly adjusted.

According to one particular embodiment, the process is carried out in an extraction column equipped with an external energy supply.

According to another embodiment, the solution of ε-caprolactam in water is prepared in situ by feeding water into the top of the column and providing for thorough mixing in the upper part of the column.

The process is generally carried out using an extraction column into which the aqueous solution of ε-caprolactam is supplied at the top. Columns with an external energy supply are particularly suitable, for example, those equipped with rotary inserts and means for pulsating the liquid column or the inserts. Pulsating columns of filling bodies, pulsating columns of sieve plates, ARD columns, Kuhni columns and Scheibel columns are particularly suitable. It is generally sufficient to carry out the process in 3 to 12 stages, depending on the desired degree of purification, but a larger number of stages may, of course, be provided if desired.

The solution of ε-caprolactam in water may be prepared beforehand or it may be prepared in situ in the upper part of the column. For in situ preparation of the solution, the water may be fed into the top of the column, but means for adequate distribution and mixing in the upper stages of the column must then be provided. Stirring or pulsation of the column is particularly suitable for this purpose. Supplying the washing liquid at a uniform rate is also advantageous.

It is not necessary to add the total quantity of aqueous ε-caprolactam solution or water from the top of the column. If desired, part of the washing liquid may be introduced into the column itself, preferably in the upper third thereof. A better concentration profile is then obtained. The washing liquid fed in at the top of the column and that fed into the upper part of the column need not have the same composition. For example, aqueous caprolactam solutions obtained from some other stage in the manufacturing process may be introduced into the upper part of the column, for example the specifically lighter layer of the mixture of ε-caprolactam and oleum neutralised with ammonia, which is obtained in the course of the Beckmann rearrangement (so-called lactam oil containing about 70% by weight of ε-caprolactam and 30% by weight of water). If desired, filtered aqueous solutions of crude caprolactam from the gas phase rearrangement of cyclohexanone oxime may equally well be used (such solutions may contain, for example, 90% by wt. of caprolactam and 10% by weight of water).

The washed solution of caprolactam in benzene, toluene or xylene may then be worked up by the usual methods. For example, the organic solvent may be removed distillation and the ε-caprolactam may then be distilled, or it may be isolated by crystallisation. It may be further purified by the usual methods.

The main advantage of the method of purification according to the invention is that it yields an organic ε-caprolactam solution which is free from salts, acids and alkalies and is therefore particularly suitable for the crystallisation of ε-caprolactam from toluene.

EXAMPLE 1

A mixture of caprolactam and sulphuric acid obtained by the Beckmann rearrangement in oleum was neutralised with ammonia and extracted with benzene. The solution of caprolactam in benzene was washed in a Scheibel column having 20 partitions. The solution of caprolactam in benzene, containing 25.2% by weight of lactam, 72.6% by weight of benzene and 2.2% by weight of water, was pumped into the column from below at the rate of 2000 ml per hour and at the same time water was introduced at the head of the column at the rate of 60 ml per hour. The speed of rotation of the stirrer was regulated so that the water was already very finely subdivided after the second partition of the upper part of the column and so that, after one third of its length, the column contained a mixture of 40% by weight of caprolactam, 50% by weight of water and 10% by weight of benzene.

The partition layer was kept below the level at which the ε-caprolactam solution in benzene was fed in, and the purified ε-caprolactam solution in benzene was discharged at the top of the column. The ε-caprolactam obtained after distillation of this solution had the following characteristics:

| | |
|---|---|
| Colour Index | 5 |
| Solidification point | 69.10° C. |
| Volatile bases | 0.3 m equ./kg |
| UV number | 95 |
| Permanganate number above | 40,000 |

The ε-caprolactam crystallised from the purified solution had the following characteristics:

| | |
|---|---|
| Colour Index | 5 |
| Solidification point | 69.10° C. |
| Volatile bases | 0.15 m equ/kg |
| UV number | 96 |
| Permanganate number above | 40,000 |

EXAMPLE 2

ε-Caprolactam obtained from the catalytic rearrangement of cyclohexanone oxime was taken up in toluene and then washed with water in a pulsating sieve bottom column. The resulting solution of ε-caprolactam in toluene (21.4% by wt. of ε-caprolactam, 75.3% by weight of toluene and 2.7% by weight of water) was fed in from the bottom at the rate of 200 kg/hour and a 50% aqueous ε-caprolactam solution was sprayed in at the head of the column at the rate of 6 kg/hour. The stroke and frequency of the pulsator were adjusted to ensure even distribution of the aqueous ε-caprolactam solution. The partition layer of the extract of washings was situated below the level at which the solution of ε-caprolactam in toluene was fed in.

Pure ε-caprolactam was obtained from the toluene extract discharged from the head of the column by crystallising this extract twice. The ε-caprolactam had the following characteristics:

| Colour index | 5 |
| --- | --- |
| Solidification point | 69.10° C. |
| Volatile bases | 0.15 m equ./kg |
| UV number | 96 |
| Permanganate number above | 40,000 |

EXAMPLE 3

The solution of ε-caprolactam in benzene used in Example 1 was washed in a 45:55 by wt. mixture of ε-caprolactam and water in an ARD column. The solution of caprolactam in benzene was fed in from the bottom at the rate of 10 m³/hour and water was sprayed in from the top of the ARD column at the rate of 300 l/hour. The benzene extract was worked up by distillation. The caprolactam obtained had the following characteristics:

| Colour index | 5 |
| --- | --- |
| Solidification point | 69.10° C. |
| Volatile bases | 0.3 m equ./kg |
| UV number | 95 |
| Permanganage number above | 40,000 |

EXAMPLE 4

ε-Caprolactam was extracted with toluene from the neutralised reaction mixture obtained from a Beckmann rearrangement, as described in Example 1. The solution in toluene was washed in a pulsating sieve bottom column with 70 shelves at 60° C. by injecting water at the head of the column and so-called lactam oil (70% by weight of ε-caprolactam, 30% by weight of water) at the 50th shelf.

| Rate of injection per hour: | |
| --- | --- |
| 70 | l of caprolactam solution in toluene (fed in from below) |
| 0.78 | l of water (at shelf No. 60) |
| 7.7 | l of lactam oil (at shelf No. 50). |

The stroke and frequency of the pulsator were adjusted to achieve the most rapid and thorough possible distribution of the two bases injected at the levels of the 50th and 60th shelf. The injection of lactam oil enables the concentration of ε-caprolactam in the discharged washed toluene extract to be maintained or increased without loss of quality.

Working up of the extract by distillation yields an ε-caprolactam having the following characteristics:

| Colour index | 5 |
| --- | --- |
| Solidification point | 69.10° C. |
| Volatile bases | 0.3 m equ./kg |
| UV number | 94 |
| Permanganate number above | 40,000 |

Comparison experiment

An experiment was carried out as described in Example 1 of German Auslegeschrift No. 1,031,308. The washed organic phase was worked up on one occasion by distillation and on another by crystallisation. The lactam obtained had the following characteristics:

| Working up by distillation | |
| --- | --- |
| Colour index | 5 |
| Permanganate number | 30,000 |
| UV number | 83 |
| Solidification point | 69.10° C. |
| Alkalinity* | 0.0001 |
| Volatile bases | 0.4 m equ./kg |
| Working up by crystallisation | |
| Colour index | 10 |
| Permanganate number | 40,000 |
| UV number | 93 |
| Solidification point | 69.10° C. |
| Alkalinity | −0.0014 |
| Volatile bases | 0.15 m equ./kg |

*0.2 % of NaOH was added during working up by distillation.

What we claim is:

1. A process for purifying a solvent solution of ε-caprolactam dissolved in benzene, toluene or xylene and containing an impurity selected from the group consisting of salts, acids and alkalies, said process comprising counter-current extracting the solvent solution in at least three stages with 5% to 50% by weight, based on the weight of the solvent solution, of a washing liquid comprising a solution of ε-caprolactam in water having an ε-caprolactam to water weight ratio of from 15:1 to 1:3 to thereby obtain a solvent solution of ε-caprolactam of reduced impurity content and an aqueous solution of ε-caprolactam containing impurities removed from said solvent solution.

* * * * *